(12) United States Patent  
Stone et al.

(10) Patent No.: US 7,758,643 B2
(45) Date of Patent: Jul. 20, 2010

(54) STABLE CARTILAGE DEFECT REPAIR PLUG

(75) Inventors: Kevin T Stone, Winona Lake, IN (US); Karen Troxel, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 56 days.

(21) Appl. No.: 11/711,178

(22) Filed: Feb. 26, 2007

(65) Prior Publication Data

US 2008/0249632 A1 Oct. 9, 2008

(51) Int. Cl.
*A61F 2/08* (2006.01)
*A61F 2/28* (2006.01)
*A61F 2/02* (2006.01)

(52) U.S. Cl. .......... 623/14.12; 623/23.61; 623/23.63; 623/23.75

(58) Field of Classification Search .......... 623/14.12, 623/23.61, 23.75, 23.76, 908
See application file for complete search history.

(56) References Cited

U.S. PATENT DOCUMENTS

| | | | |
|---|---|---|---|
| 4,185,383 A * | 1/1980 | Heimke et al. .......... 433/173 |
| 4,642,120 A | 2/1987 | Nevo et al. | |
| 5,306,311 A | 4/1994 | Stone et al. | |
| 5,607,474 A * | 3/1997 | Athanasiou et al. ...... 623/23.71 |
| 5,624,463 A | 4/1997 | Stone et al. | |
| 5,632,745 A | 5/1997 | Schwartz | |
| 6,080,194 A | 6/2000 | Pachence et al. | |
| 6,569,172 B2 | 5/2003 | Asculai et al. | |
| 6,592,598 B2 | 7/2003 | Vibe-Hansen et al. | |
| 6,592,599 B2 | 7/2003 | Vibe-Hansen et al. | |
| 6,626,950 B2 | 9/2003 | Brown et al. | |
| 6,632,246 B1 | 10/2003 | Simon et al. | |
| 6,852,125 B2 | 2/2005 | Simon et al. | |
| 6,858,042 B2 | 2/2005 | Nadler et al. | |
| 2003/0036801 A1 | 2/2003 | Schwartz et al. | |
| 2004/0162622 A1* | 8/2004 | Simon et al. ........... 623/23.5 |
| 2005/0038520 A1 | 2/2005 | Binette et al. | |
| 2005/0251268 A1* | 11/2005 | Truncale .............. 623/23.63 |
| 2008/0133008 A1* | 6/2008 | Truncale et al. ......... 623/14.12 |

* cited by examiner

*Primary Examiner*—David Isabella
*Assistant Examiner*—Yashita Sharma
(74) *Attorney, Agent, or Firm*—Harness, Dickey

(57) ABSTRACT

A method of distributing a load to a cartilage defect repair plug is provided. A load is applied to a first articulation layer. The load is distributed to a second layer and the load is transferred in the normal direction to the first density of subchondral bone. The load is distributed to a third layer and the load is transferred in the normal direction to a second density of subchondral bone. The load is then distributed to a fourth layer and the load is transferred in the normal direction to a third density of subchondral bone.

25 Claims, 5 Drawing Sheets

STABLE CARTILAGE DEFECT REPAIR PLUG

FIELD

The present teachings relate to methods and apparatus for repairing cartilage defects.

BACKGROUND

Articular cartilage enables bones to move smoothly relative to one another. Damage to the articular cartilage and the underlying bone can be caused by injury, such as tearing, by excessive wear, or by a lifetime of use. Damage to articular cartilage, particularly of the load-bearing regions may cause pain and reduce mobility. Medical intervention such as medications, therapy, or surgery can be required to restore proper function to the damaged area. In surgeries with osteochondral grafts or plugs, attention must be given to the surrounding tissue for a successful implant. The load placed on the surrounding tissue should be within an appropriate range to maintain the plug in the implant site and prevent the application of too much stress on the implant site and the underlying subchondral and/or cancellous bone. Accordingly, there is a need for an osteochondral implant which provides sufficient structural strength and minimizes the amount of healthy tissue which must be removed to accommodate the implant.

SUMMARY

The present teachings provide methods of distributing a load to a cartilage defect repair plug. A load is applied to a first articulation layer. The load is distributed to a second layer and the load is transferred in a normal direction to a first density of subchondral bone. The load is distributed to a third layer and the load is transferred in a normal direction to a second density of subchondral bone. The load is then distributed to a fourth layer and the load is transferred in a normal direction to a third density of subchondral bone.

Further areas of applicability of the present teachings will become apparent from the detailed description provided hereinafter. It should be understood that the detailed description and specific examples, while indicating the preferred embodiment of the teachings, are intended for purposes of illustration only and are not intended to limit the scope of the present teachings.

BRIEF DESCRIPTION OF THE DRAWINGS

The present teachings will become more fully understood from the detailed description and the accompanying drawings, wherein.

DETAILED DESCRIPTION

Figure 1:
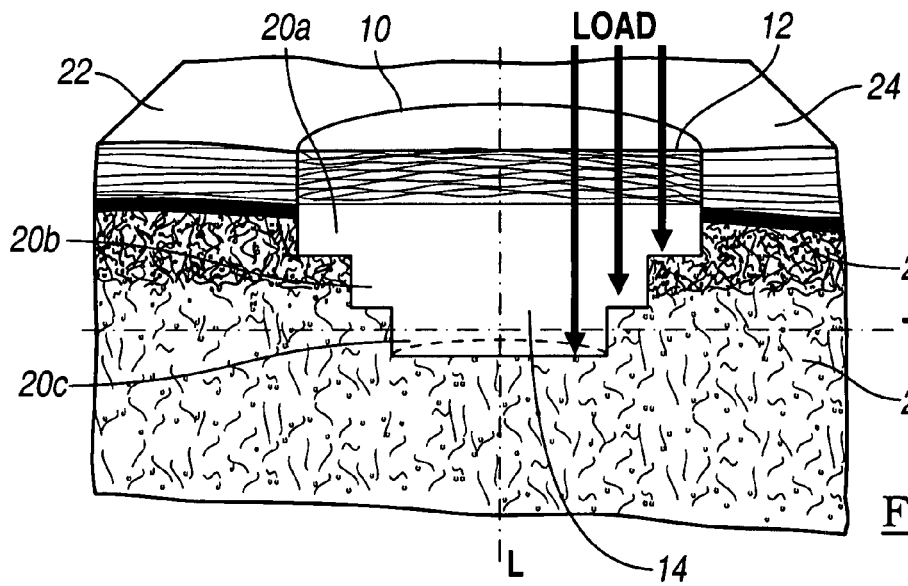
FIG. 1 depicts an environmental view of a cartilage plug according to the present teachings.
Figure 2A:
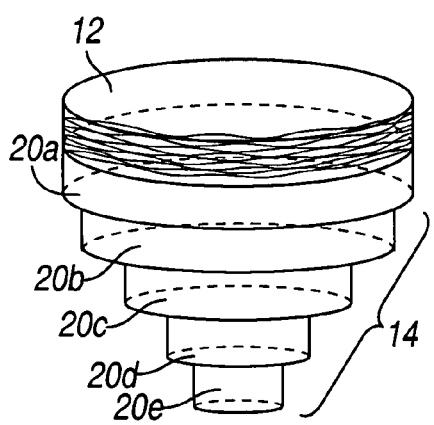
FIG. 2A through 2C depict cartilage plugs according to the present teachings.
Figure 2B:
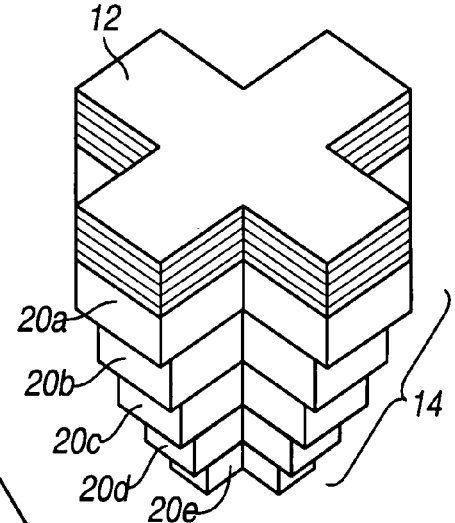
Figure 2C:
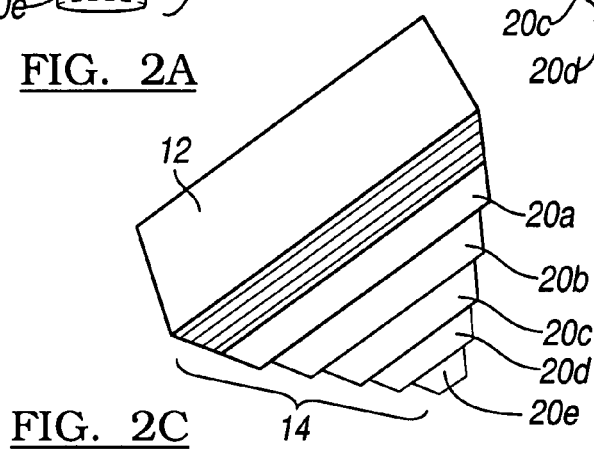
Figure 4:
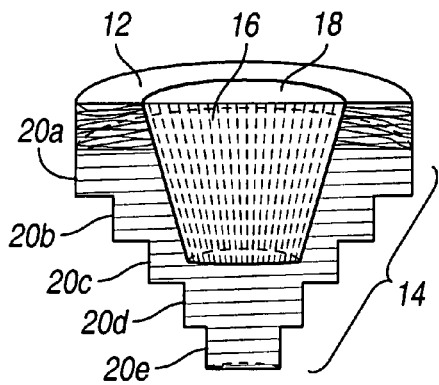
FIG. 4 depicts a cut away view of a cartilage plug containing a bioactive material according to the present teachings.

The following description of the various embodiments is merely exemplary in nature and is in no way intended to limit the present teachings, their application, or uses. It is understood that the present teachings can be used in any cartilage containing area of the body.

Referring to FIGS. 1 through 7C, a cartilage plug 10 is provided. The cartilage plug includes a top or articulation layer 12, a base 14, and optionally, a bore 16 containing a bioactive material 18 (see FIG. 4A). The plug includes a stepped shoulder geometry provided by a plurality of layers 20a, 20b, 20c, 20d, and 20e. The cartilage plug 10 is adapted to be placed in an implant site 22. The implant site 22 includes cartilage 24, a calcified cartilage interface 26, and subchondral bone 28. The implant site 22 extends along longitudinal axis L and transverse axis T. The implant site 22 can be selected from any articular cartilage region including, but not limited to, femoral condyle, tibial plateau, femoral head, acetabulum, humeral head, glenoid cavity, talus, and tarsal.

The stepped shoulder geometry of the cartilage plug 10 allows the weight or load from the cartilage plug 10 to be concentrated at the calcified cartilage interface 26 and the upper regions of the subchondral bone 28 (or the regions most proximal to the cancellous bone at the implant site 22). The layers 20a through 20e have a progressively decreasing cross-section or diameter from the articulation layer 12 (layer 20a) to the distal most end of the cartilage plug base 14 (layer 20e). The load induced by cartilage plug 10 is lightest at the distal end of the plug base 14 to minimize the load placed on the subchondral bone 28 and effectively the cancellous bone 29, which is less able to bear a heavy load as compared to the subchondral bone 28.

The stepped geometry and load distribution prevent undesired movement of the cartilage plug 10 in the implant site 22. The undesired movement can result from, for example, a load being applied to the subchondral bone 28 that deforms or partially collapses the underlying cancellous bone 29 or from the protrusion of the cartilage plug 10 above the surrounding cartilage as to interfere with smooth articulation. Additionally, the load distribution from the stepped geometry can prevent formation of cysts or voids or may cause necrosis at the implant site 22.

As shown in FIGS. 1, 2A, 3, 4, and 6, each layer 20a through 20e comprises a cylinder to form a cartilage plug 10 having a stepped cone geometry. It is understood that all of the layers 20a through 20e need not be employed in each embodiment. For example, as shown in FIG. 1, only layers 20a through 20c are employed. Although the examples and methods detailed later herein may relate to the stepped cone geometry, it is understood that any shape can be employed to form the stepped shoulder geometry. These shapes can be altered to provide a "stepped" geometry such that there is progressive reduction in the cross section of the cartilage plug 10 as measured transverse to the longitudinal axis L from the wide articulation layer 12 to the narrowest distal end of the cartilage plug base 14, such as the cruciform in FIG. 2B or the rectangle in FIG. 2C. Other exemplary suitable shapes include regular and irregular polygons and rounded shapes such as ovals. The layers 20a through 20e can be arranged to provide a 90° angle, for example, between the layers to form the shoulder. In embodiments using the 90° angle, the load is transferred in the direction normal to that layer. For example, in the layer 20a, the load is transferred normal to the direction of the subchondral bone adjacent to layer 20A. In the layer 20b, the load is transferred in the direction normal to the subchondral bone adjacent to layer 20b. As the layers progress from 20a to 20e, the density of the surrounding subchondral bone decreases. The load placed on and transferred by the bone is reduced progressively from the most dense subchondral bone 28 towards the cancellous bone 29. In other words, the normal direction of the load is indicated by the arrows in FIG. 1. The load is substantially parallel to the longitudinal axis L and perpendicular to the transverse axis T.

The cartilage plug articulation layer or top 12 generally has the largest cross section (either length or surface area) of the cartilage plug 10. The cartilage plug top 12 forms a shoulder or ledge on which the cartilage plug 10 weight is distributed and supported. The articulation layer 12 helps to suspend the cartilage plug 10 in the implant site 22. The articulation layer 12 can be adapted to receive a driver, such as a screw driver, depending on the insertion technique employed.

The articulation layer 12 can be a porous material to allow integration of cartilage with the implant. The articulation layer 12 materials can be partially or fully resorbable to accommodate ingrowth of the cartilage without sacrificing structural integrity during tissue remodeling. The articulation layer 12 can be a synthetic or non-naturally derived material. In various embodiments, the articulation layer 12 can comprise a resorbable polymer material such as lactocarbonate; polyurethane urea; polymers and copolymers of trimethylene carbonate, lactic acid, and/or glycolic acid; and combinations thereof. The articulation layer 12 can also be made of materials such as natural cartilage, chondrocyte gels, hydrogels, and combinations thereof. The articulation layer 12 can be made of a porous material, a solid, non-porous material, or a non-fibrous material.

The cartilage plug base 14 includes several smaller cross section lengths or diameters than the articulation layer or top 12. The cartilage plug base 14 comprises the layers 20a through 20e. The layers have a decreasing cross section as measured along transverse axis T to the longitudinal axis L from layer 20a to layer 20e such that the weight distribution is reduced towards the cancellous bone 29. The decreasing cross section can be measured as a cross section length or a cross section area. The decreasing periphery of each layer forms the steps or shoulders in the cartilage plug geometry. Each shoulder bears and distributes a lesser load or weight as compared to the prior layer. This minimizes the load placed at the distal most end of the cartilage plug base 14.

Figure 3:
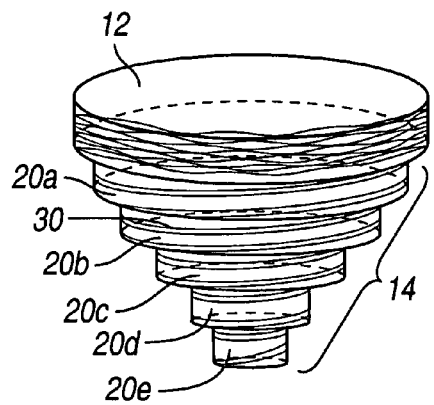
FIG. 3 depicts a cartilage plug with a bone engaging feature according to the present teachings.
Figure 5A:
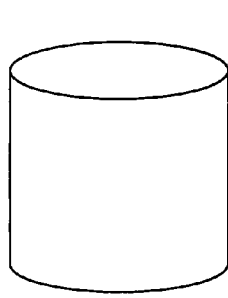
FIGS. 5A through 5C depict various shapes of the bioactive material according to the present teachings.
Figure 5B:
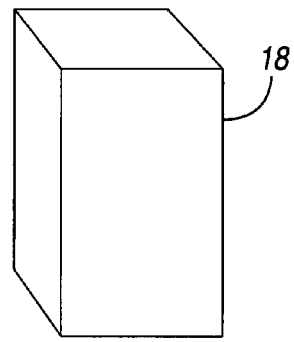
Figure 5C:
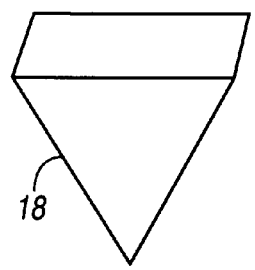

In various embodiments, the first layer 20a or upper region of the plug base 14 has substantially the same (less than 5% difference) or the same cross section as the articulation layer 12, as depicted for example in FIG. 1. A shared cross-section between the articulation layer 12 and the first layer 20a provides proper support and weight-bearing attributes to the plug in the bone. The shared cross section advantageously controls articulation height of the cartilage plug by allowing the articulation layer 12 and first layer 20a to integrate into their respective region of corresponding tissue thereby preventing the cartilage plug 10 from moving over time. Moreover, the articulation layer 12 establishes a stable articulation layer height by being configured to transfer articulation load to high density subchondral bone at substantially the same angle as an articulation load is delivered to the articulation surface. As shown in FIG. 3, for example, the layer 20a can also be smaller than the plug top 12.

The layers 20a through 20e can be generally smooth and utilize an additional securing element (suture, adhesive, etc. such as those disclosed later herein) to maintain the plug 10 in the implant site. In other embodiments, at least one layer includes at least one attachment feature to engage bone and fixedly hold the first body portion in bone. As shown in FIG. 3, the attachment feature includes threads 30. It is understood that other attachment features can be used such as one or several of a spike, pin, ridge, tooth, or another bone engaging element to fixedly hold cartilage plug 10 in the implant site 22. Various combinations of attachment features can also be used.

The cartilage plug base 14 (comprised of layers 20a through 20e or fewer layers depending on the particular cartilage plug) comprises an osteoinductive material. The cartilage plug base 14 material can be resorbable to accommodate ingrowth of new bone without sacrificing structural integrity during tissue remodeling. The cartilage plug base 14 can be a porous material such as calcium sulfate, calcium phosphate, tricalcium materials, polymers and copolymers of lactic and glycolic acid, xenograft tissue, allograft tissues, coral, demineralized bone matrix, and combinations thereof. In certain embodiments, only synthetic or non-natural materials are used to form the plug base 14.

Figure 6:
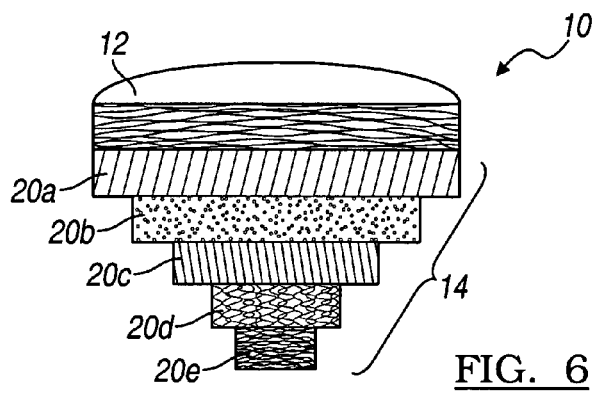
FIG. 6 depicts a cartilage plug made of a plurality of different materials.

In various embodiments, the articulation layer 12 and the cartilage plug base 14 can be made of the same material or different materials. The combination of materials can include a combination of synthetic materials. In various embodiments, the cartilage plug can comprise a synthetic articulation layer 12 and a natural base 14. In other embodiments, the cartilage plug 10 can contain a combination of different synthetic base materials. As shown in FIG. 6, the cartilage plug articulation layer 12 is made of a first material and each layer 20a through 20e of the cartilage plug base 14 is made of a different material.

To prepare the cartilage plug 10, the cartilage plug articulation layer 12 and the cartilage plug base 14 are secured together. The securing method or device can include any medically suitable securing device or technique, including, but not limited to, mechanical attachment, adhesives, chemical attachment, and combinations thereof. Mechanical attachment includes, but is not limited to, sutures, staples, tacks, nails, and the like. Adhesive attachment includes, but is not limited to fibrin glue or other bioadhesives or sealants. Chemical attachment includes cross-linking the components of the cartilage plug articulation layer 12 and the upper region of the cartilage plug base 14 together. In various embodiments, the plug articulation layer 12 and the base 14 or portions of the base can be formed from a monolithic piece of material. This is useful where the articulation layer or articulation layer 12 and the first layer 20a have substantially the same size and are made of the same material. In any of the preparations, a cartilage precursor can be adsorbed into the articulation layer 12 and a bone growth inducing material can be adsorbed into the first layer 20a.

In embodiments having a bore 16, the bore 16 can be located in any region in the cartilage plug 10 so long as the bore 16 location does not impact the load distribution. As depicted, the bore 16 is located about the central axis of the cartilage plug 10. The bore 16 can also be offset from the central axis. The bore 16 can be defined by the cartilage plug articulation layer 12 and/or the cartilage plug base 14. The bore 16 can extend from the articulation layer 12 and partially or completely through the cartilage plug base 14. The bore 16 can also be located entirely within the cartilage plug base 14 and not have a region extending into or through the articulation layer 12. The bore 16 can also extend horizontally into the articulation layer 12 and form a depression or recessed area for the bioactive material.

In certain embodiments, the bore 16 provides a void in the cartilage plug 10. The bore 16 can be filled with a bioactive material 18. The bioactive materials 18 include any material that provides a therapeutic, nutritional, or cosmetic benefit for the human or other animal subject in which the cartilage plug 10 is implanted. In various embodiments, such benefits include one or more of repairing of unhealthy or damaged tissue, minimizing infection at the implant site, increasing integration of healthy tissue into the medical implant, and preventing disease or defects in healthy or damaged tissue. Bioactive materials 18 useful in the practice of the present teachings include organic molecules, proteins, peptides, peptidomimetics, nucleic acids, nucleoproteins, antisense molecules, polysaccharides, glycoproteins, lipoproteins, carbohydrates and polysaccharides, and synthetic and biologically engineered analogs thereof, living cells such as chondrocytes, bone marrow cells, viruses and virus particles, natural extracts, and combinations thereof. Specific non-limiting examples of bioactive materials include hormones, antibiotics and other anti-infective agents, hematopoietics, thrombopoietics, agents, antiviral agents, antitumoral agents (chemotherapeutic agents), antipyretics, analgesics, anti-inflammatory agents, antiulcer agents, antiallergic agents, therapeutic agents for osteoporosis, enzymes, vaccines, immunological agents and adjuvants, cytokines, growth factors, cellular attractants and attachment agents, gene regulators, vitamins, minerals, and other nutritionals, and combinations thereof. In various embodiments, the bioactive material is advantageously selected from chondrocytes, undifferentiated cells, differentiation media, growth factors, platelet concentrate, nutrients, bone morphogenic proteins, osteogenic factors, and combinations thereof.

The bioactive agent 18 and/or the bore 16 in the cartilage plug can be of any suitable shape. The bioactive agent 18 shape can mimic the tapered shape of the cartilage plug 10 or can also be another generic shape such as those depicted in FIGS. 5A through 5C. The bioactive agent 18 can be a preformed material specific to the bore 16 or the agent 18 can be a liquid, putty, or gel which is spread in the bore 16 using a trowel or spatula.

The present teachings provide methods of preparing the cartilage plug 10. A first resorbable material having a first porosity is secured to a second resorbable material having a second porosity. The first resorbable material can comprise the articulation layer 12 and the second resorbable material can comprise at least one layer of the cartilage plug base 14. A bioactive agent is adsorbed into the first resorbable material. The materials are shaped to provide a cartilage plug 10 having a stepped shoulder geometry. A bioactive agent can be adsorbed into the first or the second resorbable material. The first resorbable material and the second resorbable material can be selected from any of the resorbable materials listed above herein. It is understood that a plurality of cartilage plug base 14 materials can be easily used by repeating the securing of multiple second resorbable materials to the cartilage plug 10.

The articulation layer 12 material can be secured to the second resorbable material using mechanical attachment, adhesive attachment, chemical attachment, and combinations thereof. For example, the articulation layer 12 material can be sewn to the cartilage plug base 14 material. If a crosslinkable polymer is used, the articulation layer 12 material and the cartilage plug base 14 material can also be crosslinked at an interface between the articulation layer 12 and the cartilage plug base 14 to secure the materials together. It may be advantageous to secure the articulation layer 12 and the cartilage plug base 14 materials together using a combination of an adhesive and a mechanical fastener, such as combination of fibrin glue and periosteal flap secured with suture.

A bioactive agent such as those disclosed earlier herein can be put into a solution or dispersion and adsorbed into either the first material and/or the second material by dipping or spraying techniques. Where a paste or gel form bioactive agent is used, the bioactive agent can be spread onto either the first or second material. The bioactive agent can also be injected into either the first material or the second material.

Shaping the cartilage plug 10 generally includes contouring the cartilage plug 10 to match an opening in an implant site 22 to provide a press-fit of the cartilage plug 10 into the implant site 22. The contouring provides the series of shoulders or ledges (or layers 20a through 20e) upon which the weight will be distributed in the implant site 22 as detailed above. To provide the shoulder, or subsequent layers having different sizes and or relative angles to the prior layer or layers, the plug can be carved from a single piece of a substrate to provide areas with peripheries of different sizes. As stated above the first layer 20a would have a first surface area and a first periphery. The second layer 20b would have a second surface area, smaller than the first surface area, and a second periphery which is smaller than the first periphery. This reduction in periphery size would continue through the layers until reaching the distal end most of the cartilage plug 10. This size difference provides the shoulder or step feature of the cartilage plug 10. Shaping the cartilage plug 10 can further include producing a bore 16 in the cartilage plug 10. In embodiments with a bore 16, the bioactive agent can be placed in the bore 16 as described earlier herein.

The cartilage plug 10 (and the optional bore 16) can be shaped using any suitable cutting tool to provide the contours desirable for appropriate fit of the cartilage plug 10 into the implant site 22. In various embodiments, a specialized tool can be used to provide a cartilage plug 10 having a stepped shoulder geometry. In still other embodiments, generic tools such as a scalpel, saw, or surgical drill can be used to shape the cartilage plug 10.

Figure 7A:
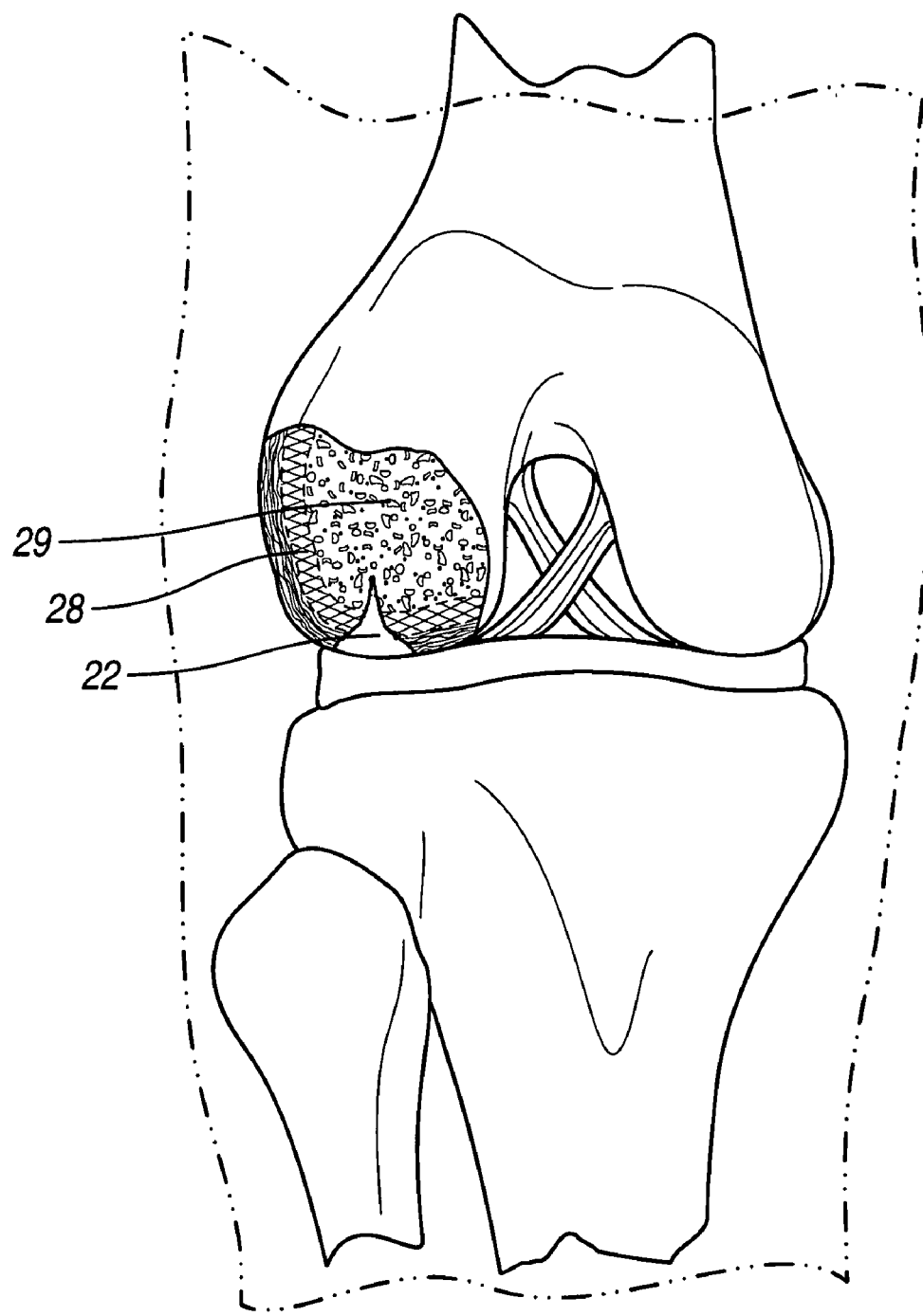
FIGS. 7A through 7C depict a process of repairing an implant site using a cartilage plug according to the present teachings.
Figure 7B:
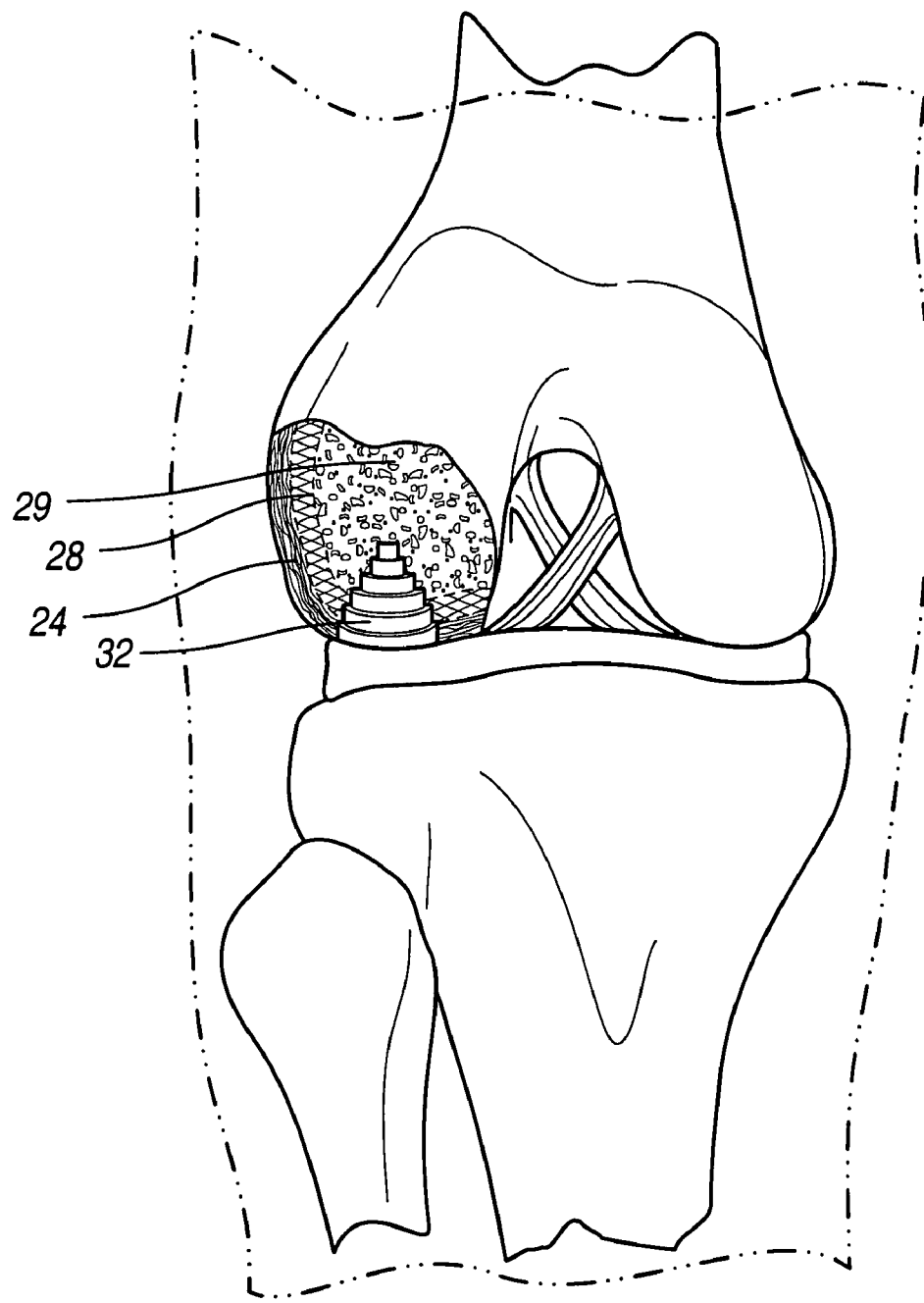
Figure 7C:
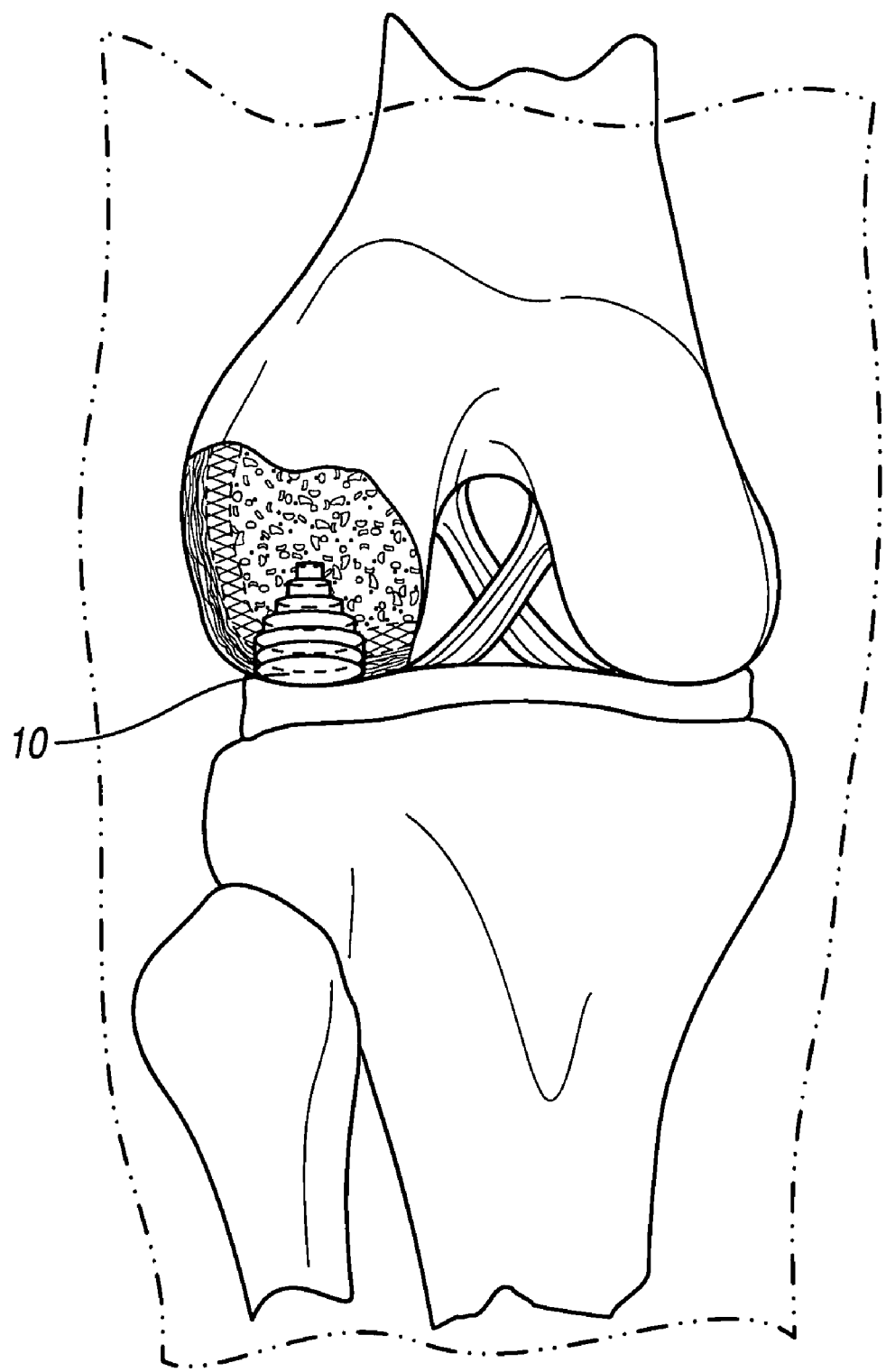

Referring to FIGS. 7A through 7C, the present teachings provide methods of repairing cartilage defects. Exemplary implant sites include, but are not limited to, a patella, a femoral condyle, a femoral head, and an acetabulum. Exemplary articular cartilage defects include those caused by trauma, excessive use (such as sports injuries, for example) or diseases, including, but not limited to, osteoarthritis and osteochondrosis dissecans. Although FIGS. 7A through 7C depict repairing a femoral condyle, the figures are merely exemplary and the surgical methods can be applied to any cartilage defect.

In various embodiments, the method of repairing the cartilage defects includes preparing the implant site 22 to form a shaped implant site 32, delivering a cartilage plug 10 to the shaped implant site 32, securing the cartilage plug 10 in the site, and delivering a bioactive agent to the shaped implant site 32.

To prepare the implant site 22, a region of cartilage 24 and underlying subchondral bone 28 tissue is removed from an implant site. The removed tissue has a progressively decreasing cross-sectional length or diameter from the cartilage to the underlying subchondral bone to provide a stepped shoulder geometry at the implant site 22. The implant site 22 can be shaped by the surgeon to provide the appropriate fit for the cartilage plug 10. The implant site 22 can be prepared by removing the damaged cartilage with a burr, a curette, or a similar instrument. Once the damaged cartilage is removed down to the calcified cartilage, the size of the defect to prepare as subchondral bone is determined. The edges of host cartilage 24 should accommodate a secure press-fit or interference fit of the cartilage plug 10 in the implant site 22. Bone is removed with a surgical drill or other cutting instrument that creates an opening having the same shape, size, and depth as the cartilage plug 10 including the stepped shoulder geometry. A specialized drill bit having a shape mated to the cartilage plug 10 can be used to provide the opening in the implant site 22. Because each cartilage defect and patient are different, the cartilage plug 10 can be additionally shaped if needed by shaving or otherwise trimming the cartilage plug 10 with a scalpel, surgical drill, or other cutting or resecting devices. The shaped implant site 32 can be cleaned to provide a healthy tissue base upon which to place the cartilage plug 10.

The cartilage plug 10, such as those detailed above, is delivered to the shaped implant site 32. The cartilage plug 10 can be delivered to the shaped implant site 32 by impaction, screwing, or press-fit techniques. The cartilage plug 10 is inserted into the shaped implant site 32 through the surrounding cartilage and bone such that the articulation layer 12 of the cartilage plug 10 is arranged generally flush with the cartilage 24 of the surrounding tissue. A flush cartilage plug 10 facilitates appropriate articulation in the region.

The cartilage plug 10 is then secured into the implant site 22. Securing the cartilage plug to the implant site can be achieved using mechanical means, adhesives, and combinations thereof, as described above herein. The cartilage plug can also be secured by press-fit or by driving a mechanical post or nail through the cartilage plug 10 and into the underlying tissue.

In embodiments having a bioactive agent, the bioactive agent is released from the bore 16 and into the implant site to facilitate tissue ingrowth into the implant site. In embodiments where the cartilage plug 10 has an additional bioactive agent adsorbed into a layer of the cartilage plug 10, that bioactive agent can elute from the cartilage plug 10 at the same time or a different time interval than the bioactive agent in the bore 16.

In other embodiments, the methods of cartilage repair generally include preparing the implant site 22 to form a shaped implant site 32, delivering the resorbable cartilage plug 10 to the shaped implant site 32, securing the cartilage plug 10 in the shaped implant site 32, and delivering a bioactive agent to the site.

Preparation of the implant site 22 includes removal of the cartilage 24 and subchondral bone 28 according to the techniques as disclosed above. A resorbable synthetic cartilage plug 10 is passed through the surrounding cartilage 24 and bone 28 and is disposed in the shaped implant site 32.

The cartilage plug 10 can be arranged in the shaped implant site 32 such that a load from the cartilage plug 10 (via the cartilage articulation layer 12) is placed on an interface between the cartilage region 24 and the subchondral bone 28. The interface can comprise at least one of the cartilage 24, the calcified cartilage 26, or the proximal most layers of the subchondral bone 28.

Arrangement of the cartilage plug 10 provides better tissue organization into the cartilage plug 10 in the shaped implant site 32. Tissue organization and ingrowth of tissue into the cartilage plug 10 are partly controlled by signals from the surrounding healthy tissue. When the tissue is placed under stress (such as from too much load or weight placed on a region of the tissue close to the cancellous bone), new tissue will not be created or become integrated into the cartilage plug 10 because the biochemical signals released from the surrounding tissue will attempt to promote enhancing strength of the subchondral bone by producing more subchondral bone adjacent to the cancellous bone to protect the cancellous bone instead of producing more subchondral bone to infiltrate the cartilage plug base 14. Accordingly, the load distribution increases tissue formation in the shaped implant site 32. The tissue organization can also be increased by matching the resorption of the cartilage plug to an ingrowth rate of the adjacent subchondral bone or an ingrowth rate of the adjacent cartilage. This helps to provide consistent structural strength to the shaped implant site 32.

The cartilage plug 10 can be secured to the shaped implant site 32 using an attachment method such as mechanical attachment, including, but not limited to sutures, adhesives, and combinations thereof. An examplary combination of multiple attachment means includes the use of a membrane to secure the cartilage plug 10 into the implant site. The membrane can include, but is not limited to, periosteal flap or hydrogel chitosan. Placing the membrane over the articulation layer 12 will assist in retaining the cartilage plug 10 in the shaped implant site 32 and serve as a protective barrier to prevent any unintentional dislodging of the cartilage plug 10. If there is a space between the membrane and the articulation layer or top 12, the space can be filled in or leveled with a fluid, such as sterile water or saline, for example. The membrane can be attached to the implant site (for example, to the surrounding cartilage 24) using an additional securing method. For example, the periosteal flap can be sutured to the shaped implant site 32 and then a fibrin sealant can be applied over the sutures.

The description of the present teachings is merely exemplary in nature and, thus, variations that do not depart from the gist of the present teachings are intended to be within the scope of the present teachings. Such variations are not to be regarded as a departure from the spirit and scope of the present teachings.

What is claimed is:

1. A method of preparing a cartilage defect repair plug that extends along a longitudinal axis for distributing a load at a cartilage defect site, comprising:

a. shaping a first layer to define a first shoulder having a first bearing surface perpendicular to the longitudinal axis of the cartilage plug and being bound by a first wall parallel to the longitudinal axis of the cartilage plug;

b. shaping a second layer to define a second shoulder having a second bearing surface perpendicular to the longitudinal axis of the cartilage plug and being bound by a second wall parallel to the longitudinal axis of the cartilage plug, said second shoulder spaced apart from said first shoulder in a direction towards said longitudinal axis; and c. shaping a third layer to define a third shoulder having a third bearing surface perpendicular to the longitudinal axis of the cartilage plug and being bound by a third wall parallel to the longitudinal axis of the cartilage plug, said third shoulder spaced apart from said second shoulder in a direction towards said longitudinal axis;

wherein when a load is applied on the cartilage plug, the load is distributed in a direction normal to the cartilage defect site;

wherein each of said first, second and third bearing surfaces and walls directly engage said cartilage defect site; and wherein the first layer includes an upper and lower layer, the upper layer being formed from a first material and configured to engage cartilage and the lower layer being formed from a second, different material and configured to engage bone, the upper and lower layers having the same width in a direction perpendicular to the longitudinal axis such that the periphery of each layer forms part of the first wall, the lower layer being disposed below the upper layer such that an upper side of the lower layer abuts the upper layer and an opposite lower side of the lower layer in a direction along the longitudinal axis abuts the second layer, the first layer being sized to extend from a region of cartilage at the cartilage defect site to a region of underlying bone at the defect site.

2. The method of claim 1, further comprising adsorbing a bioactive agent into at least one of the first layer, the second layer, and the third layer.

3. The method of claim 1, further comprising securing the first layer, the second layer, and the third layer together, wherein the securing is selected from the group consisting of: mechanical attachment, adhesive attachment, chemical attachment, and combinations thereof, and wherein the first, second and third layers include first, second and third synthetic resorbable layers.

4. The method of claim 1, further comprising contouring the cartilage defect repair plug to match an opening in an implant site to provide a press-fit of the cartilage defect repair plug into the implant site.

5. The method of claim 1, further comprising removing a region of at least one of the first layer, the second layer, and the third layer to form a bore in the cartilage defect repair plug.

6. The method of claim 5, further comprising depositing a bioactive material in the bore for delivery to the implant site, the deposited bioactive material having a top surface formed planar with a top surface of the repair plug; wherein the bioactivst e material is selected from the group consisting of: chondrocytes, undifferentiated cells, differentiation media, growth factors, platelet concentrate, nutrients, bone morphogenic proteins, osteogenic factors, and combinations thereof.

7. A method of preparing a cartilage defect repair plug that extends along a longitudinal axis for distributing a load at a cartilage defect site, comprising:
   a. shaping a first resorbable layer to define a first shoulder having a first bearing surface perpendicular to the longitudinal axis of the cartilage plug and being bound by a first wall parallel to the longitudinal axis of the cartilage plug, wherein the first wall has a smooth and cylindrical periphery;
   b. shaping a second resorbable layer to define a second shoulder having a second bearing surface perpendicular to the longitudinal axis of the cartilage plug and being bound by a second wall parallel to the longitudinal axis of the cartilage plug, wherein the second wall has a smooth, cylindrical periphery and a diameter less than a diameter of the first wall; and
   c. shaping a third resorbable layer to define a third shoulder having a third bearing surface perpendicular to the longitudinal axis of the cartilage plug and being bound by a third wall parallel to the longitudinal axis of the cartilage plug, wherein the third wall has a smooth, cylindrical periphery and a diameter less than a diameter of the second wall;
   wherein when a load is applied on the cartilage plug, the load is distributed in a direction normal to the cartilage defect site, and wherein each of said first, second and third bearing surfaces and walls directly engage said cartilage defect site;
   wherein the first resorbable layer includes an upper and a lower layer, the upper layer being formed from a first material and configured to engage cartilage and the lower layer being formed from a second, different material and configured to engage bone, the upper and lower layers having the same width in a direction perpendicular to the longitudinal axis such that the periphery of each layer forms part of the first wall, the lower layer being disposed below the upper layer such that an upper side of the lower layer abuts the upper layer and an opposite lower side of the lower layer in a direction along the longitudinal axis abuts the second layer, the first resorbable layer being sized to extend from a region of cartilage at the cartilage defect site to a region of underlying bone at the defect site.

8. The method of claim 7, further comprising adsorbing a bioactive agent into at least one of the first resorbable layer, the second resorbable layer, and the third resorbable layer.

9. The method of claim 7, further comprising securing the first resorbable layer, the second resorbable layer, and the third resorbable layer together, wherein the securing is selected from the group consisting of: mechanical attachment, adhesive attachment, chemical attachment, and combinations thereof.

10. The method of claim 7, further comprising contouring the cartilage defect repair plug to match an opening in an implant site to provide a press-fit of the cartilage defect repair plug into the implant site.

11. The method of claim 7, further comprising removing a region of at least one of the first resorbable layer, the second resorbable layer, and the third resorbable layer to form a bore in the cartilage defect repair plug, wherein the first, second and third resorbable layers include first, second and third synthetic resorbable layers.

12. The method of claim 11, further comprising depositing a bioactive material in the bore for delivery to the implant site; wherein the bioactive material is selected from the group consisting of: chondrocytes, undifferentiated cells, differentiation media, growth factors, platelet concentrate, nutrients, bone morphogenic proteins, osteogenic factors, and combinations thereof.

13. A method of preparing a cartilage defect repair plug that extends along a longitudinal axis for distributing a load at a cartilage defect site, comprising:
   a. shaping a first synthetic resorbable layer comprising at least two different materials to define a first shoulder having a first bearing surface perpendicular to the longitudinal axis of the cartilage plug and being bound by a first wall parallel to the longitudinal axis of the cartilage plug, wherein the first wall has a smooth and cylindrical periphery;
   b. shaping a second synthetic resorbable layer to define a second shoulder having a second bearing surface perpendicular to the longitudinal axis of the cartilage plug and being bound by a second wall parallel to the longitudinal axis of the cartilage plug, wherein the second wall has a smooth, cylindrical periphery and a diameter less than a diameter of the first wall;
   c. shaping a third synthetic resorbable layer to define a third shoulder having a third bearing surface perpendicular to the longitudinal axis of the cartilage plug and being bound by a third wall parallel to the longitudinal axis of the cartilage plug, wherein the third wall has a smooth, cylindrical periphery and a diameter less than a diameter of the second wall;
   d. forming a bore extending from at least a region of the first synthetic resorbable layer into a region of the second synthetic resorbable layer; and
   e. disposing a bioactive agent within the bore;
   wherein the first layer is sized to extend from a region of cartilage at the cartilage defect site to a region of an underlying bone at the cartilage defect site such that when a load is applied on the cartilage plug, the load is distributed in a direction normal to the cartilage defect site and in a direction normal to each of the first bearing surface, the second bearing surface, and the third bearing surface, and each of said first, second and third bearing surfaces and walls directly engage said cartilage defect site;

wherein the first synthetic resorbable layer includes an upper and a lower layer, the upper layer being formed from a first material and configured to engage cartilage and the lower layer being formed from a second, different material and configured to engage bone, the upper and lower layers having the same width in a direction perpendicular to the longitudinal axis such that the periphery of each layer forms part of the first wall, the lower layer being disposed below the upper layer such that an upper side of the lower layer abuts the upper layer and an opposite lower side of the lower layer in a direction along the longitudinal axis abuts the second layer.

14. The method of claim 13, further comprising adding additional layers to said cartilage plug, wherein each layer defines a shoulder having a bearing surface perpendicular to a longitudinal axis of the cartilage plug and being bound by a wall parallel to the longitudinal axis of the cartilage plug.

15. The method of claim 13, wherein the first synthetic resorbable layer, the second synthetic resorbable layer, and the third synthetic resorbable layer are each formed of different materials.

16. The method of claim 13, wherein the bore is centered about the longitudinal axis of the cartilage defect repair plug.

17. The method of claim 13, further comprising extending the bore into a region of the third synthetic resorbable layer.

18. The method of claim 13, further comprising shaping the first synthetic resorbable layer, the second synthetic resorbable layer, and the third synthetic resorbable layer from a monolithic substrate.

19. The method of claim 1, further comprising shaping the first layer, the second layer, and the third layer into a shape selected from the group consisting of: a cylinder, a cruciform, and a triangle.

20. The method of claim 1, further comprising shaping the first layer, the second layer, and the third layer from a monolithic substrate.

21. The method of claim 1, wherein the first layer, the second layer, and the third layer are made of at least two different materials and further comprising securing the at least two different materials together.

22. The method of claim 1, further comprising distributing a load on the cartilage plug in a direction normal to the first bearing surface, the second bearing surface, and the third bearing surface.

23. The method of claim 1, further comprising shaping the first layer to have a thickness greater than a thickness of at least one of the second layer and the third layer.

24. The method of claim 1, further comprising shaping the cartilage plug to provide a stepped cone geometry.

25. The method of claim 13, wherein the first, second and third synthetic resorbable layers are concentrically stacked to form a stepped cone geometry.

* * * * *

UNITED STATES PATENT AND TRADEMARK OFFICE
CERTIFICATE OF CORRECTION

| | | |
|---|---|---|
| PATENT NO. | : 7,758,643 B2 | Page 1 of 1 |
| APPLICATION NO. | : 11/711178 | |
| DATED | : July 20, 2010 | |
| INVENTOR(S) | : Stone | |

It is certified that error appears in the above-identified patent and that said Letters Patent is hereby corrected as shown below:

Column 9, Line 27, Claim 6
"bioactivst" should be -- bioactive --

Column 9, Line 59, Claim 7
insert -- layer -- after upper

Column 11, Line 5, Claim 13
insert -- layer -- after first occurrence of upper

Signed and Sealed this
Twenty-sixth Day of June, 2012

David J. Kappos
*Director of the United States Patent and Trademark Office*